United States Patent [19]

Katsuyama et al.

[11] Patent Number: 4,503,145

[45] Date of Patent: *Mar. 5, 1985

[54] QUANTITATIVE ANALYSIS FILM

[75] Inventors: Harumi Katsuyama; Yoshikazu Amano; Asaji Kondo, all of Asakashi, Japan

[73] Assignee: Fuji Photo Film Co., Ltd., Kanagawa, Japan

[*] Notice: The portion of the term of this patent subsequent to Oct. 23, 2001 has been disclaimed.

[21] Appl. No.: 352,970

[22] Filed: Feb. 26, 1982

[30] Foreign Application Priority Data

Feb. 27, 1981 [JP] Japan .................... 56-28159

[51] Int. Cl.³ ............ G01N 33/52; C12Q 1/28; C12Q 1/52
[52] U.S. Cl. ............................ 435/16; 422/56; 435/28; 435/805
[58] Field of Search .......... 435/16, 25, 28, 805; 422/56, 57, 58; 436/66, 95, 170, 135

[56] References Cited

U.S. PATENT DOCUMENTS 3,867,258  2/1975  Forgione ............ 435/805 X
4,042,335  8/1977  Clement ................ 422/56
4,153,668  5/1979  Hill et al. ............. 422/56
4,166,093  8/1979  Smith-Lewis et al. ..... 422/56
4,246,342  1/1981  Misaki et al. .......... 435/25
4,260,679  4/1981  Tsuda et al. .......... 436/95 X
4,316,954  2/1982  Snoke et al. .......... 435/25 X

FOREIGN PATENT DOCUMENTS 55-0111799  8/1980  Japan .................. 435/25
56-122947   9/1981  Japan .................. 435/28

Primary Examiner—Arnold Turk
Attorney, Agent, or Firm—Sughrue, Mion, Zinn, Macpeak, and Seas

[57] ABSTRACT

An analysis film for assaying transaminase activity comprises a reagent layer containing pyruvic acid oxidase, a combination of a hydrogen donor and a coupler—which is capable of forming a cationic dye—and an anionic polymer. The cationic dye formed by the reaction with a color indicator composition for detecting hydrogen peroxide is fixed with the anionic polymer, thereby mobilization and diffusion of the cationic dye being prevented so that the analysis film achieves high detection sensitivity and high accuracy.

7 Claims, 8 Drawing Figures

QUANTITATIVE ANALYSIS FILM

BACKGROUND OF THE INVENTION

1. Field of the Invention

The present invention relates to a quantitative analysis film for quantitatively assaying transaminase activity and more particularly to a quantitative analysis film comprising a reagent layer containing a substrate for transaminase, pyruvic acid oxidase and a color indicator composition for detecting hydrogen peroxide, for quantitative assay for transaminase activity.

A method for assaying various transaminase activities which comprise directly producing pyruvic acid by reacting various transaminases with the corresponding substrates, or producing pyruvic acid indirectly through a chemical reaction(s) in which other enzyme(s) participate or through a chemical reaction(s) in which no enzyme participates, reacting the thus produced pyruvic acid with pyruvic acid oxidase and a color indicator composition for detecting hydrogen peroxide which contains peroxidase and then measuring pyruvic acid colorimetrically is known and disclosed in, e.g., Japanese Patent Application (OPI) No. 13068/80. The method as disclosed in this specification involves a series of chemical reactions in an aqueous solution and requires accurate weighing or voluming and complicated handling of an aqueous solution and such accordingly requires long periods of time for analytical operation. Such a method is still insufficient as a method for clinical investigations requiring speed in analysis and accuracy in analytical results.

2. Development of the Invention

Various quantitative analysis films, particularly multilayered analysis films which permit colorimetric analysis of hydrogen peroxide by dry procedures, have been proposed and some of them have been put in practical use. Among them, there are quantitative analysis films for analysis of glucose, uric acid, cholesterol, choline esterase, creatine, etc., in the living body by a dry procedure which comprises, in sequence, reacting the same with the appropriate oxidizing enzyme or reacting the reaction product formed during an enzyme reaction with the appropriate oxidizing enzyme, reacting the thus released hydrogen peroxide with a color indicator to form color, and then measuring the formed color. In order to enhance the speed of examination, avoid complicated operation and reduce cost, demands for dry type quantitative analysis films have increased, particularly in the field of clinical examination. Thus, quantitative analysis films of the test paper sheet type of the single layer or multi-layer quantitative analysis type of high accuracy in analysis have been developed.

In particular, multi-layer composite type quantitative analysis films are disclosed in Japanese Patent Application (OPI) (the term "OPI" as used herein refers to a "published unexamined Japanese patent application) No. 53888/74 (corresponding to U.S. Pat. No. 3,992,158; hereafter the same have markedly improved accuracy in analysis as compared to conventional quantitative analysis films of the test paper sheet type having a single or dual layers. For purposes of further improving accuracy in analysis and in accordance with the analyte to be assayed, hydrogen peroxide indicators having high detection sensitivity have also been provided in such multi-layer composite type quantitative analysis forms; examples of indicators for detecting hydrogen peroxide and layer structures for such multi-layer analysis films are disclosed in Japanese Patent Applications (OPI) Nos. 40191/76 (corresponding to U.S. Pat. No. 4,042,335), 131089/78, 29700/79 (corresponding to U.S. Pat. No. 4,166,093), 124499/80, etc.

Indicators for detecting hydrogen peroxide used for these quantitative analysis films by a dry procedure are based on those for detecting hydrogen peroxide employed in conventional quantitative analysis by a dry procedure and the principles are the same.

The normal range for transaminase values in a normal human is approximately 20 IU/l at maximum in whole blood and an amount of a substrate which undergoes a catalytic action of transaminase during a time period for several ten minutes required for measurement methods conventionally employed is a concentration of $10^{-4}$ mole/l even under optimal conditions. For effecting a colorimetric measurement of such a trace amount of a substrate through coupled enzyme reactions, it is required that: (1) respective reactions sufficiently proceed, (2) light extinction of a dye formed is large, (3) a dye is stable until it is measured and (4) in the case where a colorimetric measurement is performed using a quantitative analysis film, a produced dye is not lost by the dye being mobilized or diffused until it is measured. As a result of extensive investigations, it has been found that by selecting such a system that the reaction product is converted into hydrogen peroxide via pyruvic acid by transaminase enzyme reaction or a combination of transaminase enzyme reaction with other enzyme reaction(s) coupled with transaminase enzyme reaction, by selecting as a color indicator system for detecting hydrogen peroxide such a system that a cationic dye is produced and by the use of 4-aminoantipyrine or an N,N-disubstituted-p-phenylenediamine as a hydrogen donor and an N,N-disubstituted aniline derivative as a coupler in combination, high reaction efficiency, large light extinction of a produced cationic dye and markedly high sensitivity in transaminase activity measurement are obtained.

SUMMARY OF THE INVENTION

An object of the present invention is to provide a quantitative analysis film capable of measuring transaminase activity by a dry procedure.

Another object of the present invention is to provide a quantitative analysis film capable of measuring transaminase activity having high detection sensitivity by producing a cationic dye having high extinction of light using a color indicator for detecting hydrogen peroxide and then colorimetrically determining the dye.

A further object of the present invention is to provide a quantitative analysis film having high detection sensitivity capable of measuring transaminase activity with high accuracy by producing a cationic dye having high extinction of light using a color indicator for detecting hydrogen peroxide and preventing mobilization and diffusion of the dye.

The present invention is directed to:

(1) A quantitative analysis film comprising a reagent layer containing pyruvic acid oxidase.

Main embodiments include:

(2) A quantitative analysis film as described in (1) wherein the reagent layer further contains a substrate for transaminase.

(3) A quantitative analysis film as described in (1) or (2) wherein the reagent layer further contains a phosphate-source compound, flavine adenine dinucleotide, thiamine pyrophosphate, a divalent or trivalent metal ion and a color indicator composition for detecting hydrogen peroxide.

(4) A quantitative analysis film as described in (3) wherein the color indicator composition for detecting hydrogen peroxide comprises a substance having peroxidase activity, a hydrogen donor and a coupler.

(5) A quantitative analysis film as described in (4) wherein the hydrogen donor and the coupler are a combination capable of forming a cationic dye and the reagent layer further contains the anionic polymer.

(6) A quantitative analysis film as described in any one of (1) to (5) wherein the reagent layer is composed of a single layer.

(7) A quantitative analysis film as described in any one of (1) to (5) wherein the reagent layer is composed of at least two layers comprising a transaminase substrate layer containing a substrate for transaminase.

(8) A quantitative analysis film as described in any one of (1) to (5) wherein the reagent layer is composed of at least two layers comprising a dye-fixing layer containing a substrate for transaminase.

(9) A quantitative analysis film as described in any one of (1) to (5) wherein the reagent layer is composed of at least three layers comprising a transaminase substrate layer containing a substrate for transaminase and a dye-fixing layer containing an anionic polymer; and

(10) A quantitative analysis film as described in any one of (1) to (9) wherein a support is provided on one side of the reagent layer and a porous layer on the other side, and the porous layer is adhered to the reagent layer in fluid contact as a united or integral composite.

BRIEF DESCRIPTION OF THE DRAWINGS

In FIGS. 1 through 8, numerals are used to mean:
10: support
20: reagent layer
21: POP-color forming reaction-dye fixing layer
22: TA substrate-POP-color forming reaction layer
23: TA substrate layer
24: dye fixing layer
25: reagent-impregnated support
31: porous spreading layer
32: definite area-porous layer
40: light reflecting layer

PREFERRED EMBODIMENTS OF THE INVENTION

Figure 1:
FIGS. 1 through 8 show outlined cross sections of embodiments of the analysis film in accordance with the present invention.

Various transaminases, the activity of which can be measured in accordance with the present invention, are known. Of these, glutamyl pyruvate transaminase (GPT) and glutamyl oxaloacetate transaminase (GOT) are of importance.

GPT and GOT are enzymes for catalyzing the following reactions, respectively:

Quantitative assay for activities of GPT and GOT plays an important role in diagnosis of liver diseases since increased concentrations of GPT and GOP in blood are a measure of liver diseases.

As pyruvic acid oxidase (hereafter referred to as "POP") used in the present invention, any enzyme can be employed as far as it catalyzes reactions that form acetylphosphoric acid, carbon dioxide and hydrogen peroxide from pyruvic acid, inorganic phosphoric acid and oxygen; preferred examples include POP obtained by cultivation of bacteria belonging to the Pediococcus genus, bacteria belonging to the Streptococcus genus and bacteria belonging to the Aerococcus genus. A method for collecting POP is described in, e.g., Japanese Patent Application (OPI) No. 13068/80. POP is commercially available and easily accessible.

POP requires (1) a phosphate-source compound, (2) co-enzymes (thiamine pyrophosphate and flavine adenine dinucleotide) and (3) heavy metal ions, as is well known in the art. For effecting POP activity, these three components are necessary in addition to POP. In the specification, a composition comprising a phosphate-source compound, co-enzymes, heavy metal ions and POP is referred to as a POP composition.

Phosphate-source compounds are compounds capable of providing or releasing phosphate ions and are well established in the art. As phosphate-source compounds, phosphate ions $PO_4^{3-}$, phosphate ions containing acidic hydrogen ($HPO_4^{2-}$, $H_2PO_4^{-}$), acids thereof or salts thereof can be employed. Phosphoric acid esters or complexes thereof that can release phosphate ions or phosphate ions containing acidic hydrogen through hydrolysis can also be employed. Specific examples of phosphate-source compounds include phosphoric acid ($H_3PO_4$), trisodium phosphate, hydrogen disodium phosphate, dihydrogen sodium phosphate, tripotassium phosphate, hydrogen dipotassium phosphate, dihydrogen potassium phosphate, hydrogen aluminum phosphate, hydrogen calcium phosphate, manganese phosphate, hydrogen manganese phosphate, hydrogen magnesium phosphate, hydrogen iron phosphate, hydrogen cobalt phosphate, etc. Phosphate-source compounds can also be used as phosphate buffer solutions. Phosphoric acid-source compounds can be used in a range of from 0.1 μmole to 10 μmoles, preferably 0.3 μmole to 5 μmoles, as calculated to phosphate ions, based on 1 U (an activity for forming 1 μmole of hydrogen peroxide for 1 minute at 37° C. is defined to be 1 unit(U)) of POP.

Flavine adenine dinucleotide (hereafter simply referred to as "FAD") can be employed in a range of from 0.1 nmole to 50 nmoles, preferably 0.3 nmole to 30 nmoles, based on 1 U of POP.

As thiamine pyrophosphates (TPP), thiamine diphosphate (TDP) or thiamine triphosphate (TTP) can be employed; of these, thiamine diphosphate is preferred. Thiamine pyrophosphate can be used in a range of from 5 nmoles to 500 nmoles, preferably 10 nmoles to 300 nmoles, based on 1 U of POP.

Divalent or trivalent metal ions are divalent or trivalent metal ions that can activate the activity of POP; specific examples include $Ca^{2+}$, $Co^{2+}$, $Mg^{2+}$ and $Al^{3+}$. These metal ions can also be employed as salts or com-

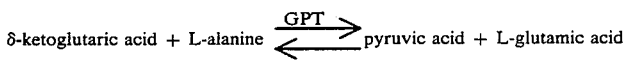

(3)

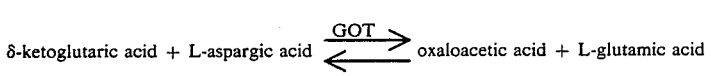

(4)

plexes thereof that contain and can release these metal ions. In the case that phosphates or hydrogen phosphates are employed as salts containing divalent or trivalent metal ions, the phosphate source compound and the divalent or trivalent metal ions can be covered by a single compound common thereto. Examples of salts containing divalent or trivalent metal ions include chlorides, sulfates, nitrates, phosphates, hydrogen sulfates, hydrogen phosphates, carbonates, hydrogen carbonates and acetates. Preferred metal ions are $Mn^{2+}$ and $Mg^{2+}$ and preferred metal salts are chlorides, phosphates and hydrogen phosphates. Specific examples of preferred metal salts are manganese (II) chloride, manganese(II) phosphate, manganese (II) hydrogen phosphate, magnesium (II) chloride and magnesium (II) hydrogen phosphate. The divalent or trivalent metal ions can be employed in an amount ranging from 5 nmoles to 10 nmoles, preferably 10 nmoles to 5 μmoles, based on 1 U of POP.

The color indicator composition for detecting hydrogen peroxide can be appropriately chosen from indicators capable of colorimetrically measuring a color formed (change in color or color formation) or fluorescence. In the quantitative analysis film of the present invention, it is preferred that a cationic dye-forming color indicator for detecting hydrogen peroxide capable of forming a cationic dye by a chemical interaction in the presence of hydrogen peroxide be employed as the color indicator for detecting hydrogen peroxide and an anionic polymer be employed in combination therewith.

In the specification, the term "reagent layer" is used to refer to a layer in which an analyte is converted into a chemically detectable species and which contributes to improvement in detection efficiency of the chemically detectable species. The reagent layer further optionally contains a cationic dye-forming color indicator composition for detecting hydrogen peroxide and an anionic polymer.

The term "color-forming reaction layer" refers to a layer in which an analyte is converted into a chemically detectable species.

The term "dye-fixing layer" refers to a layer which contributes to improvement in detection efficiency of the chemically detectable species.

The reagent layer can be a TA substrate (later defined), color-forming reaction and dye-fixing layer when the reagent layer is a single layer and the reagent layer can also be divided into two or more layers, one of which is a TA substrate layer and others are a dye-fixing layer, a color forming reaction layer, etc. In other words, a TA substrate layer, a color-forming reaction layer, a dye-fixing layer, etc., can also be collectively referred to as a reagent layer.

The chemically detectable species is directly or indirectly indicative of the presence and/or concentration of a desired analyte, or a reaction or decomposition product of the analyte.

The term "substance having peroxidase activity" is used to mean a substance which catalyzes oxidation of a hydrogen donor with hydrogen peroxide (as a substrate) and such is well recognized in the art (I. Yamazaki et al., *MOLECULAR & CELLULAR BIOCHEMISTRY*, vol. 2(1), pp. 39–52 (1973)). The substance having peroxidase activity takes part in the oxidation of a hydrogen donor with hydrogen peroxide in accordance with the following reation scheme:

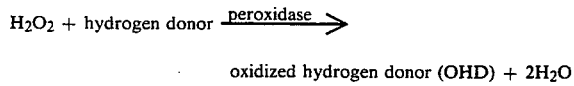

The term "hydrogen donor" refers to a compound which is an oxygen acceptor which, in its oxidized state, couples with the N,N-disubstituted anilines of formula (1).

The cationic dye-forming color indicator composition for detecting hydrogen peroxide containing a component capable of producing a cationic dye by chemical interaction in the presence of hydrogen peroxide (hereafter referred to as a "color indicator for detecting hydrogen peroxide") is an indicator composition comprising, as main ingredients, a substance having peroxidase activity, a hydrogen donor and an N,N-disubstituted aniline.

Examples of substances having peroxidase activity include peroxidase extracted from various organisms, synthetic peroxidase and other chemical substances extracted from organisms which exhibit an activity similar to peroxidase, as disclosed in Japanese Patent Application (OPI) 137192/75. Of these, peroxidase is preferred.

As hydrogen donors which are contained in the color indicator, 4-substituted antipyrines (4-substituted-2,3-dimethyl-1-phenyl-3-pyrazolin-5-ones) as disclosed in Japanese Patent Application (OPI) No. 50991/74 (corresponding to U.S. Pat. No. 3,983,005) and other known 4-substituted antipyrines; N,N-disubstituted-o- or p-phenylenediamines as disclosed in Japanese Patent Application (OPI) No. 137192/75 (corresponding to U.S. Pat. No. 3,886,045) and other known N,N-disubstituted-o- or p-phenylenediamines; 2-hydrazonobenzothiazolines as disclosed in Japanese Patent Application (OPI) No. 20471/80 and other known 2-hydrazonobenzothiazolines; p-halogenophenols as disclosed in Japanese Patent Application (OPI) No. 148100/80 and other p-halogenophenols and N,N-disubstituted phenylenediamines as represented by formula (2) below can be employed.

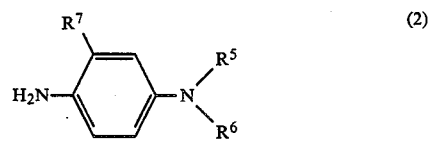

(2)

wherein $R^5$ and $R^6$ represent an alkyl group, an alkoxyalkyl group, a hydroxyalkyl group, a cyanoalkyl group, a halogenoalkyl group or an acylaminoalkyl group and, $R^5$ and $R^6$ may be the same or different; $R^7$ represents a hydrogen atom, an alkyl group, an alkoxy group or a halogen atom.

Specific examples of useful 4-substituted antipyrines include 4-aminoantipyrine (CAS Registry Number (83-07-8); hereafter the same), 4-(dimethylamino)antipyrine (pyramidon (58-15-1), 4-(ethylaminoantipyrine) (15166-10-6)), 4-(methylamino)antipyrine (noramidopyrine, (519-98-2)), 4-(sodium sulfonatomethylamino)antipyrine (sulphamipyrine (129-89-5)); 4-((sodiumsulfonatomethyl) (isobutyl)amino antipyrine (dibupyrone (1046-17-9)), 4-(sodium sulfonatomethyl)(methyl)amino antipyrine (methampyrone, (5907-38-0)) and 4-isopropylantipyrine (propiphenazone, (479-92-5)). As other compounds having a similar structure, there are 4-amino-2,3-dimethyl-1-p-tolyl-3-pyrazolin-5-one (56430-10-5) and 4-amino-1,3-diphenyl-2-methyl-3-pyrazolin-5-one (52744-73-7). Also, 2-(dimethylamino)-5-phenyl-2-oxazolin-4-one (tozalinone, (1046-17-9)) can be employed.

In the case where substituents $R^5$ and $R^6$ in N,N-disubstituted-p-phenylenediamines represented by formula (2) are an alkyl group, the alkyl group can be a straight or branched lower alkyl group having 1 to 5 carbon atoms; specific examples thereof include a methyl group, an ethyl group, a propyl group, a butyl group, a pentyl group, an isopropyl group, an isobutyl group, an isoamyl group, a t-butyl group and a neopentyl group. In the case of an alkoxyalkyl group, the alkoxyalkyl group comprises a lower alkyl group having 1 to 3 carbon atoms on which a lower alkoxy group having 1 to 3 carbon atoms is substituted; specific examples include a methoxymethyl group, a 2-methoxyethyl group, a 1-methoxyethyl group, a 3-methoxypropyl group, a 2-methoxypropyl group, an ethoxypropyl group and a 2-ethoxyethyl group. In the case of a hydroxyalkyl group, the hydroxyalkyl group comprises a straight or branched lower alkyl group having 1 to 5 carbon atoms on which a hydroxyl group is substituted; specific examples include a hydroxymethyl group, a 2-hydroxyethyl group, a 1-hydroxyethyl group, a 3-hydroxypropyl group, a 2-hydroxypropyl group, a 4-hydroxybutyl group and a 5-hydroxypropyl group. In the case of a cyanoalkyl group, the cyanoalkyl group comprises a straight or branched lower alkyl group having 1 to 5 carbon atoms on which a cyano group is substituted; specific examples thereof include a cyanomethyl group, a 2-cyanoethyl group, a 1-cyanoethyl group, a 3-cyanopropyl group, a 2-cyanopropyl group and a 5-cyanopentyl group. In the case of a halogenoalkyl group, the halogenoalkyl group comprises a straight or branched lower alkyl group having 1 to 5 carbon atoms on which a fluorine, chlorine, bromine or iodine atom is substituted as a halogen atom; specific examples thereof include a fluoromethyl group, a chloromethyl group, a bromomethyl group, a 2-fluoroethyl group, a 1-chloroethyl group, a 2-chloroethyl group, a 2-bromoethyl group and a 3-chloropropyl group. In the case of an acylaminoalkyl group, the acylaminoalkyl group comprises a straight or branched lower alkyl group having 1 to 5 carbon atoms on which an acetamido group, a propionamido group, a benzamido group, a toluamido group, a methanesulfonamido group, a benzenesulfonamido group or a toluenesulfonamido group is substituted as an acylamino group (1 to 10 carbon atoms); specific examples include an acetamidomethyl group, a propionamidomethyl group, a benzamidomethyl group, a p-toluamidomethyl group, a methanesulfonamidomethyl group, an ethanesulfonamidomethyl group, a benzenesulfonamidomethyl group, a p-toluenesulfonamidomethyl group, a 2p-acetamidoethyl group, a 2-propionamidoethyl group, a 2-benzamidoethyl group, a 2-p-toluamidoethyl group, a 2-methanesulfonamidoethyl group, a 2-(ethanesulfonamido) ethyl group, a 2-(benzenesulfonamido)ethyl group, a 2-(p-toluenesulfonamido)ethyl group, a 3-acetamidopropyl group and a 3-benzamidopropyl group.

Specific examples of preferred $R^5$ and $R^6$ groups include a methyl group, an ethyl group; a methoxymethyl group, a 2-methoxyethyl group, an ethoxymethyl group, a 2-ethoxyethyl group; a hydroxymethyl group, a 2-hydroxyethyl group, a 1-hydroxyethyl group, a 2-hydroxypropyl group; an acetamidomethyl group, a 2-acetamidoethyl group, a methanesulfonamidomethyl group, a 2-methanesulfonamidoethyl group; a chloromethyl group, a 2-chloroethyl group; a cyanomethyl group and a 2-cyanoethyl group.

In the case substituent $R^7$ in N,N-disubstituted-p-phenylenediamines represented by formula (2) is an alkyl group, specific examples thereof are the same as the specific examples in the case where $R^5$ and $R^6$ are an alkyl group. In the case $R^7$ is an alkoxy group, the alkoxy group is an alkoxy group which comprises a straight or branched lower alkyl group having 1 to 5 carbon atoms and specific examples include a methoxy group, an ethoxy group, a propoxy group, an isopropoxy group, a butoxy group, an isobutoxy group, a pentyloxy group and an isoamyloxy group. In the case $R^7$ is halogen atom, specific examples include a fluorine atom, a chlorine atom, a bromine atom and an iodine atom.

Preferred substituents as $R^7$ are a hydrogen atom, an alkyl group (1 to 5 carbon atoms) and a halogen atom; the alkyl group is specifically a methyl group, an ethyl group or a propyl group and the halogen atom is specifically a fluorine atom or a chlorine atom.

Specific examples of N,N-disubstituted-p-phenylenediamines represented by formula (2) include the following compounds:

N,N-Dimethyl-p-phenylenediamine
N,N-Diethyl-p-phenylenediamine
N-Ethyl-N-(β-hydroxyethyl)-p-phenylenediamine
N-Ethyl-N-(β-ethoxyethyl)-p-phenylenediamine
N-Ethyl-N-(β-methanesulfonylaminoethyl)-3-methyl-4-aminoanilinine
N-Ethyl-N-(β-hydroxyethyl)-3-methyl-4-aminoaniline
N-Ethyl-N-(β-cyanoethyl)-p-phenylenediamine
N-Ethyl-N-(β-chloroethyl)-p-phenylenediamine
N-Ethyl-N-(β-ethoxyethyl)-p-phenylenediamine
N,N-Diethyl-3-chloro-4-aminoaniline
N,N-Bis(β-cyanoethyl)-p-phenylenediamine As hydrogen donors, 4-substituted antipyrines and N,N-disubstituted-p-phenylenediamines represented by formula (2) are preferred. Of these, 4-aminoantipyrine, N,N-dimethyl-p-phenylenediamine and N,N-diethyl-p-phenylenediamine are particularly preferred.

N,N-Disubstituted anilines are compounds represented by formula (1) below:

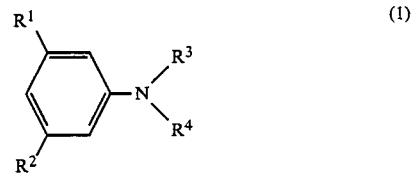

In formula (1), $R^1$ and $R^2$ each represents a hydrogen atom, an alkyl group or an alkoxy group and $R^1$ and $R^2$ may be the same or different from each other; $R^3$ and $R^4$ represent an alkyl group, an alkoxyalkyl group, a hydroxyalkyl group, an aminoalkyl group, a cyanoalkyl group, a halogenoalkyl group or an acylaminoalkyl group and $R^3$ and $R^4$ may be the same or different from each other.

In the case substituents $R^1$ and $R^2$ in the N,N-disubstituted aniline represented by formula (1) represent an alkyl group or an alkoxy group, specific examples thereof are the same as the specific examples in the case that substituents $R^5$ or $R^6$ in the N,N-disubstituted-p-phenylenediamine represented by formula (2) described above represent an alkyl group or an alkoxy group.

In the case $R^3$ and $R^4$ represent an alkyl group, an alkoxyalkyl group, a hydroxyalkyl group, a cyanoalkyl group, a halogenoalkyl group or an acyalminoalkyl group, specific examples thereof are the same as the specific examples in the case where $R^5$ or $R^6$ represent an alkyl group, an alkoxyalkyl group, a hydroxyalkyl group, a cyanoalkyl group, a halogenoalkyl group on an acylaminoalkyl group. In the case $R^3$ and $R^4$ represent an aminoalkyl group, the aminoalkyl group comprises a straight or branched lower alkyl group having 1 to 5 carbon atoms on which an amino group is substituted; specific examples include an aminomethyl group, a 2-aminoethyl group, a 1-aminoethyl group, a 3-aminopropyl group and a 2-aminopropyl group.

Preferred substituents as $R^1$ and $R^2$ are a hydrogen atom, an alkyl group (1 to 5 carbon atoms) and an alkoxy group (1 to 3 carbon atoms); specific examples of the alkyl group are a methyl group, an ethyl group, a propyl group and, as the alkoxy group, there are a methoxy group and an ethoxy group.

Preferred substituents as $R^3$ or $R^4$ are an alkyl group, an alkoxyalkyl group, a hydroxyalkyl group, a cyanoalkyl group and a halogenoalkyl group; specific examples include a methyl group, an ethyl group, a propyl group; a methoxymethyl group, a 2-methoxyethyl group, a 3-methoxypropyl group, an ethoxymethyl group, a 2-ethoxyethyl group; a hydroxymethyl group, a 1-hydroxyethyl group, a 2-hydroxyethyl group, a 2-hydroxypropyl group, a 3-hydroxypropyl group; a cyanomethyl group, a 2-cyanoethyl group; a chloromethyl group, a 1-chloroethyl group, a 2-chloroethyl group, a 2-chloropropyl group, a 3-chloropropyl group, a bromomethyl group, a 2-bromomethyl group, a fluoromethyl group and a 2-fluoroethyl group.

Specific examples of N,N-disubstituted anilines represented by formula (1) include the following compounds:
N,N-Dimethylaniline
N,N-Diethylaniline
N-Methyl-N-hydroxymethylaniline
N-Methyl-N-(2-hydroxyethyl)aniline
N-Ethyl-N-(2-hydroxyethyl)aniline
N-Methyl-N-(2-methoxyethyl)aniline
N-Ethyl-N-(2-methoxyethyl)aniline
N-Ethyl-N-(2-ethoxyethyl)aniline
N,N-Dimethyl-m-toluidine
N,N-Diethyl-m-toluidine
N,N-Bis(hydroxymethyl)-m-toluidine
N,N-Bis(2-hydroxyethyl)-m-toluidine
N,N-Bis(2-hydroxypropyl)-m-toluidine
N,N-Bis(3-hydroxypropyl)-m-toluidine
N-Methyl-N-hydroxymethyl-m-toluidine
N-Ethyl-N-2-hydroxyethyl-m-toluidine
N-Ethyl-N-hydroxymethyl-m-toluidine
N-Methyl-N-methoxymethyl-m-toluidine
N-Ethyl-N-methoxymethyl-m-toluidine
N-Ethyl-N-2-methoxyethyl-m-toluidine
N-Cyanomethyl-N-hydroxymethyl-m-toluidine
N-Methyl-N-2-chloroethyl-m-toluidine
N-Ethyl-N-2-chloroethyl-m-toluidine
N-2-Cyanoethyl-N-2-hydroxyethyl-m-toluidine
N,N-Dimethyl-m-anisidine Of these compounds, preferred N,N-disubstituted anilines are the following:
N,N-Bis(2-hydroxyethyl)-m-toluidine
N-Ethyl-N-2-hydroxyethyl-m-toluidine
N-2-Cyanoethyl-N-2-hydroxyethyl-m-toluidine
N,N-Dimethyl-m-anisidine
N,N-Diethyl-m-anisidine The anionic polymer employed in the present invention is a polymer containing an anionic group in the polymer backbone itself or the organic group (Org in Formula (AP)) bound to the polymer backbone. In addition to conventional anionic polymers, acid type cation ion exchange resins can also be employed as the anionic polymer; preferably the conventional anionic polymers or cation ion exchange resin are water-soluble polymers or polymers which are capable of being swollen by water (water-swellable). The anionic polymers can be employed singly or as a combination of two or more. Anionic polymers with and without film forming capability can both be employed but it is preferred that anionic polymers having no film-forming capability be employed in combination with binder polymers having film forming capability.

Specific examples of anionic polymers include polymers or copolymers having a structure where a carboxylate group (—COO$^\ominus$), a sulfonate group (—SO$_3^\ominus$) or a phosphonate group (—PO$_3^{2\ominus}$) is bound as an anionic atomic group, or the aforesaid anionic atomic group containing a counter cation is bound to all of the constitutional repeating units (hereafter referred to as "CRU") of the high molecular chain thereof or to a part of the CRU (the arrangement may be either orderly or at random). As counter cations, there are alkali metal ions (e.g., Li$^\oplus$, Na$^\oplus$, Cs$^\oplus$), alkaline earth metal ions (e.g., Mg$^{2\oplus}$, Ca$^{2\oplus}$, Sr$^{2\oplus}$, Ba$^{2\oplus}$) and ammonium ions (NH$_4^\oplus$).

These anionic polymers are shown by formula (AP):

Org—Q—Z$^\ominus$A$^\oplus$ (AP)

wherein Org represents an organic group and constitutes a portion of a polymer backbone, Q represents a chemical bond(s) or a chemical group linking Z$^\oplus$ to Org, Z$^\oplus$ represents a carboxylate group; (—COO$^\oplus$), a sulfonate group (—SO$_3^\oplus$) or a phosphonate group (—PO$_3^{2\oplus}$) and A$^\ominus$ is a counter cation as mentioned above.

Specific examples of anionic polymers containing the aforesaid CRU include the following:

Alkali hydrolysates of a methyl vinyl ether-maleic anhydride copolymer (copolymer containing dilithium, disodium or dipotassium 1,2-dicarboxylate ethylene as the CRU);

Alkali metal salt or alkaline earth metal salt of a polyacrylic acid;

Alkali metal salt or alkaline earth metal salt of a poly-N-($\beta$-sulfo-$\alpha,\alpha$-dimethylethyl)acrylamide;

Alkali metal salt or alkaline earth metal salt of a polystyrene-p-sulfonic acid;

Alkali metal salt or alkaline earth metal salt of a copolymer of styrene-p-sulfonic acid and a hydrophilic vinyl monomer (examples of hydrophilic vinyl monomers: acrylic acid, acrylic acid alkyl esters (e.g., methyl acrylate), acrylic acid hydroxyalkyl esters (e.g., $\beta$-hydroxyethyl acrylate), acrylamides (e.g., acrylamide, N-methylacrylamide, N-isopropylacrylamide, N-($\beta$-sulfonato-$\alpha,\alpha$-dimethylethyl)acrylamide, N-ethyl-N-isopropylacrylamide, acrylmorpholide

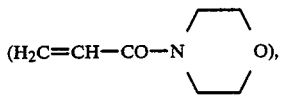

N-acryloylpiperidine, N-acryloylpiperidine, N-acryloylpiperazine), methacrylic acid hydroxyalkyl esters (e.g., β-hydroxyethyl methacrylate), methacrylamides (e.g., methacrylamide, methacrylmorpholide));

Alkali metal salts of a polyvinylphosphonic acid:

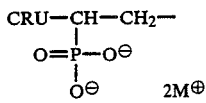

where M is lithium, sodium or potassium; Carboxymethyl cellulose; Carboxethyl cellulose; Alginic acid and alkali metal salts thereof;

Typical examples of preferred anionic polymers include the following:
Polystyrene-p-potassium sulfonate
Styrene-p-potassium sulfonate-acrylmorpholide copolymer
Styrene-p-potassium sulfonate-acrylamide copolymer
Styrene-p-potassium sulfonate-N-isopropylacrylamide copolymer
Styrene-p-sodium sulfonate-N-ethyl-N-isopropylacrylamide copolymer
Poly-N-(β-potassium sulfonato-α,α-dimethyl)acrylamide
N-(β-potassium sulfonato-α,α-dimethylethyl)acrylamide-β-hydroxyethyl acrylate copolymer
N-(β-potassium sulfonato-α,α-dimethylethyl)acrylamide-N-ethylacrylamide copolymer Of these anionic polymers, polystyrene type anionic polymers (in formula (AP), Q is a phenylene group) are most preferred.

The anionic polymer can be incorporated into a layer containing the color indicator for detecting hydrogen peroxide or a dye-fixing layer containing the anionic polymer—but containing no other reagent component—and can also be provided as a layer separately from a layer containing the color indicator for detecting hydrogen peroxide. Further, the anionic polymer can also be incorporated both into a layer containing the color indicator for detecting hydrogen peroxide and into the dye-fixing layer. The anionic polymer can also be employed as a combination of two or more thereof if desired or necessary, although only one is generally sufficient.

In the case that the anionic polymer is incorporated both into a layer containing the color indicator for detecting hydrogen peroxide and into the dye-fixing layer, both anionic polymers can be the same or they can differ. Further, if desired or necessary, the anionic polymer can also be incorporated into a layer other than a layer containing the color indicator for detecting hydrogen peroxide or a dye-fixing layer.

For quantitatively determining transaminase activity, various substrates for transaminase (hereafter referred to as a "TA substrate") or compositions containing a TA substrate (hereafter referred to as a "TA substrate composition") are contained in the analysis film of the present invention. In the case that the transaminase is glutamyl-pyruvate transaminase (GPT), the TA substrate is used as a combination of alanine and α-ketoglutaric acid; in the case of glutamyl-oxaloacetate transaminase (GOT), as a combination of aspargic acid and α-ketoglutaric acid; and in the case of assay for GOT activity, oxaloacetate decarboxylase is further employed in addition thereto, by which GOT acts on its substrate as a catalyst and the resulting oxaloacetic acid (or a salt thereof) is then decarboxylated to produce pyruvic acid (or a salt thereof). The TA substrate or TA substrate composition (hereafter collectively referred to as a "TA substrate composition") can be incorporated into the same layer as that containing the POP composition or into a separate layer. In the case where the TA substrate composition and the POP composition are incorporated into the same layer, both compositions can be simply mixed or both can be located in the same layer after separately pulverizing both compositions.

In the present specification, the reagent layer is used to mean both a single reagent layer containing four elements composed of the TA substrate composition, the POP composition, a color indicator for detecting hydrogen peroxide and an anionic polymer and collectively a plurality of layers containing any one of the aforesaid compositions, etc., and further including a structure-assisting layer(s) and/or an analytical function-assisting layer(s) optionally provided depending upon necessity. A layer referred to in the specification is generally expressed by indicating a composition or a compound incorporated into the layer; that is, a layer containing the TA substrate composition is referred to as a TA substrate layer, a layer containing the POP composition as a POP layer, a layer containing the color indicator for detecting hydrogen peroxide as a color forming reaction layer, a layer containing an anionic polymer layer as a dye fixing layer, a layer containing three of the POP composition, the color indicator for detecting hydrogen peroxide and an anionic polymer as a POP-color forming reaction-dye fixing layer, a layer containing the POP composition and the color indicator for detecting hydrogen peroxide as a POP-color forming reaction layer, a layer containing the color indicator for hydrogen peroxide and an anionic polymer as a color forming reaction-dye fixing layer, a layer containing three of the TA substrate composition, the POP composition and the color indicator for detecting hydrogen peroxide as a TA substrate-POP-color forming reaction layer, and the like.

In the analysis film of the present invention, a single reagent layer containing four of the TA substrate composition, the POP composition, the color indicator for detecting hydrogen peroxide and an anionic polymer can be provided and at least four layers composed of a TA substrate layer containing the TA substrate composition, a POP layer containing the POP composition, a color forming reaction layer containing the color indicator for detecting hydrogen peroxide and a dye fixing layer containing an anionic polymer can be provided. Further, two layers composed of a TA substrate layer and a POP-color forming reaction-dye fixing layer containing three of the POP composition, the color indicator for detecting hydrogen peroxide and an anionic polymer can be provided. As such, the number (a single layer to four or more layers) of the reagent layer and location thereof can be appropriately chosen depending upon kinds of transaminase to be assayed, ingredients contained in the analysis film, and the utility or accuracy required for the analysis film.

When a combination of the hydrogen donor and the coupler contained in the analysis film of the present invention is capable of forming a cationic dye, the cationic dye represented by formula (CD):

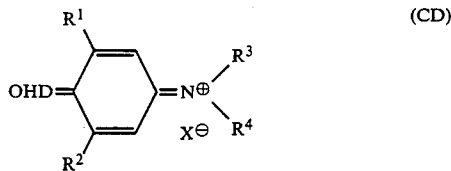

wherein $R^1$ through $R^4$ have the same meanings as in formula (1), $X^{\ominus}$ represents an anion and OHD represents the oxidized hydrogen donor moiety, is formed when a liquid sample is dropped onto the analysis film, and the cationic dye is then fixed by an anionic polymer further contained in the analysis film.

In the analysis film of the present invention, it is preferred that a binder polymer be incorporated into a layer(s) free of anionic polymers. However, a binder polymer can also be incorporated into a layer(s) containing anionic polymers. As binder polymers, known hydrophilic polymers can be employed. Specific examples of hydrophilic polymers include gelatin, casein, agarose, starch, polyvinyl alcohol, polyvinyl pyrrolidone, polyacrylamide, polyethylene glycol, etc. Conventional hardeners (hardening agents or cross linking agents) can also be employed together with hydrophilic polymers. Each of the aforesaid layers can be provided by coating a solution or dispersion containing the corresponding composition or component(s) onto a support in accordance with known coating methods and then drying. Further, the surface or interior of a porous support can also be impregnated with a solution or dispersion containing the corresponding composition or component(s) to exhibit a similar effect. In this case, binder polymers can often be omitted. In the case that these layers are provided onto a support by a coating technique, the thickness of a reagent layer is generally between 3 μm and 100 μm, preferably between 5 μm and 50 μm when it is a single layer; in the case of a combination of two or more layers, the thickness of each layer is generally between 1 μm and 50 μm, preferably 2 μm and 30 μm.

The analysis film in accordance with the present invention can take various layer structures depending upon use, accuracy required for quantitative assay, etc. The present invention will be explained below with reference to the drawings showing preferred embodiments of the present invention.

FIG. 1 is an analysis film comprising a reagent-impregnated support 25 obtained by impregnating the surface and interior of a self-supporting porous support with all of the TA substrate composition, the POP composition, the color indicator for detecting hydrogen peroxide and an anionic polymer.

As self-supporting porous supports, known film-like or sheet-like supports such as a filter paper, conventional paper, non-woven cloth, membrane filter, porous plastic film, etc., can be employed. In the case that the quantitative analysis film is to be installed in a slide frame as disclosed in Japanese Patent Application (OPI) Nos. 156079/79 and 160296/79, Japanese Utility Model Application No. 41787/80 (Japanese Utility Model Application (OPI) No. 142454/81). Japanese Patent Application No. 138100/80 (Japanese Patent Application (OPI) No. 63452/82), etc., flexible materials such as fabrics can also be employed in addition to the materials described above as the porous support. Such a quantitative analysis film can be employed by adhering it onto a film-like or sheet-like support using a hot melt adhesive or an adhesive tape and the layer structure in this case is similar to that of a quantitative analysis film shown in FIG. 2, which will subsequently be described.

Figure 2:
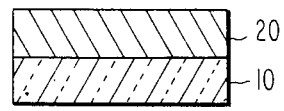

FIG. 2 shows a quantitative analysis film having such a structure that reagent layer 20 containing four of the TA substrate composition, the POP composition, the color indicator for detecting hydrogen peroxide and the anionic polymer is provided on film-like or sheet-like support 10. The support 10 can be either transparent or opaque.

Figure 3:
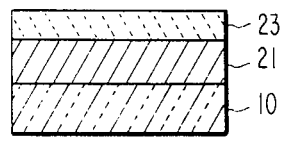

FIG. 3 shows a quantitative analysis film having such a structure that POP—color forming reaction—dye fixing layer 21 containing three of the POP composition, the color indicator for detecting hydrogen peroxide and the anionic polymer and TA substrate layer 23 containing the TA substrate composition are provided, in this sequence, on a film-like or sheet-like support. The support can be either transparent or opaque but it is preferably a transparent support.

In quantitative analysis films as shown in FIG. 4 through FIG. 8, a reagent layer, a TA substrate layer, a color-forming reaction layer, a color forming reaction-dye fixing layer or a dye-fixing layer is provided between a support and a porous layer and the porous layer is brought into fluid contact (this definition is disclosed in Japanese Patent Application (OPI) No. 40191/76, ESP Application No. 0013156, etc., described above i.e., a mode of contact using the ability of a fluid, whether liquid or gaseous, to pass between layers) with the reagent layer, the TA substrate layer, the color-forming layer, the color forming reaction-dye fixing layer or the dye-fixing layer; preferably, the analysis film has such a structure that these layers are adhered in a unitary or integral form.

The porous layer is employed as a porous spreading layer or a definite area-porous layer which have the function that when a sample liquid is spotted thereon the sample liquid is supplied onto a layer therebeneath and preferably has the function of rendering the quantity of the liquid sample per unit area approximately constant (in the case of the porous spreading layer), or which has the function of spreading into the same area of its shape to thereby render the quantity of the liquid sample per unit area approximately constant (in the case of the definite area-porous layer), in both cases the liquid sample being supplied to a layer therebeneath.

Another embodiment can comprise impregnating the interior of a porous layer (a porous spreading layer or definite area-porous layer) with the TA substrate composition, without providing a TA substrate layer as an independent separate layer. The porous layer has a definite area which is determined so that a liquid sample can be supplied thereto in an amount greater than that of water which can be held in the porous layer, and is often referred to as "definite area-porous layer", as described above.

Figure 4:
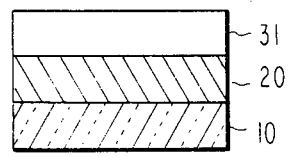

FIG. 4 shows an analysis film having a layer structure comprising a film-like or sheet-like support 10 having provided thereon, in sequence, reagent layer 20 containing four of the TA substrate composition, the POP composition, the color indicator for detecting hydrogen peroxide and an anionic polymer and porous spreading layer 31.

Figure 5:
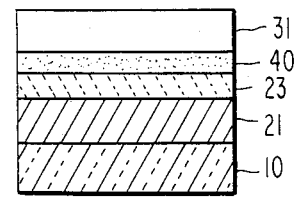

FIG. 5 shows an analysis film having a layer structure comprising film-like or sheet-like support 10 having provided thereon, in sequence, POP-color forming reaction dye fixing layer 21 containing three of the POP composition, the color indicator and an anionic polymer, TA substrate layer 23 containing the TA substrate composition, light reflecting layer (or light blocking layer) 40 and porous spreading layer 31.

As the porous spreading layer of the quantitative analysis film shown in FIG. 4 or FIG. 5, a porous layer having dispersed therein finely divided porous powders such as blush polymers (generally called, membrane filters), diatomaceous earth, microcrystalline materials (e.g., microcrystalline cellulose (Avicel, tradename of FMC Corporation)) in a binder polymer, porous aggregates formed by allowing fine spherical beads of glass or polymers to adhere to one another in point to point contact; a non-fibrous isotropic porous layer such as an aggregated three-dimensional lattice particle structure formed by allowing fine spherical beads of water-non-swellable organic polymers to adhere to one another using a water-insoluble adhesive in point-to-point contact, etc., as disclosed in Japanese Patent Application (OPI) No. 90589/80; a fibrous anisotropic layer comprising fabrics rendered hydrophilic as disclosed in Japanese Patent Application (OPI) No. 164356/80, fabrics which are rendered physically hydrophilic (e.g., by a glow discharge, a plasma treatment, corona discharge, ultraviolet irradiation, a flame treatment etc.) as disclosed in Japanese Patent Application (OPI) No. 140532/80, filter paper, etc.; can be employed.

The method for providing a non-fibrous isotropic porous layer onto reagent layer 20 or light-reflecting layer 40 as a porous spreading layer can be in accordance with the techniques disclosed in Japanese Patent Application (OPI) Nos. 53888/74, 90589/80, etc., described above or a method for providing the fibrous anisotropic porous spreading layer onto reagent layer 20 or light-reflection layer 40 as a porous spreading layer can be in accordance with the techniques disclosed in Japanese Patent Application (OPI) No. 164356/80 and Japanese Patent Application No. 140532/80 described above.

The constant area porous layer can be provided using materials (e.g., fabrics, paper, membrane filters) and in accordance with the method disclosed for the porous layer in Japanese Utility Model Application No. 120299/80. As materials for the constant area porous layer, the same materials as used for the porous spreading layer can be employed and, in addition thereto, any material can be employed so long as the interior of the material is porous and can retain a liquid such as water and the pores thereof penetrate from one major surface to the other major surface. The method for providing the constant area porous layer onto a reagent layer, a light-reflecting layer, or the like can be in accordance with the method disclosed in Japanese Utility Model Application No. 120299/80 or the method for providing the porous spreading layer described above.

As light-reflecting layer 40, a layer having dispersed one or more white pigments such as finely divided titanium dioxide powder, finely divided barium sulfate powder or the like in a hydrophilic binder polymer as disclosed in Japanese Patent Application (OPI) Nos. 53888/74, 40191/76, 164356/80, etc., a blush polymer layer (membrane filter) having dispersed therein one or more white pigments such as finely divided titanium dioxide powder, finely divided barium sulfate powder or the like as disclosed in Japanese Patent Application (OPI) No. 53888/74, etc., a blush polymer layer as disclosed in Japanese Patent Application (OPI) No. 53888/74, etc., a water-permeable layer comprising a porous metal layer as disclosed in Japanese Patent Application (OPI) No. 26428/80, a water-permeable layer containing one or more metal powders as disclosed in Japanese Patent Application (OPI) No. 26429/80, etc., can be employed; techniques for providing these layers can be in accordance with the methods as disclosed in the specifications described above.

Figure 6:
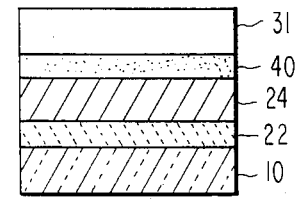

FIG. 6 indicates an analysis film having a layer structure comprising support 10 having provided thereon, in sequence, TA substrate-POP-color forming reaction layer 22 containing three of the TA substrate composition, the POP composition and the color indicator for detecting hydrogen peroxide, dye fixing layer 24 containing an anionic polymer, light reflecting layer 40 and porous spreading layer 31. As long as a cationic compound that interfers with colorimetric analysis by absorbing light in the wavelengh region which the resulting cationic dye absorbs is not contained in the color indicator for detecting hydrogen peroxide, the relative location of a layer containing the TA substrate composition, the POP composition or the color indicator for detecting hydrogen peroxide to a dye fixing layer can be freely chosen. Accordingly, the layer structure as shown in FIG. 6 is particularly advantageous in the case where a layer containing the TA substrate composition, the POP composition or the color indicator for detecting hydrogen peroxide is desired to be provided as a lower layer so as not to contact with air, for the reason that the color indicator for detecting hydrogen peroxide contains a component(s) which might be oxidized by air, etc.

Figure 7:
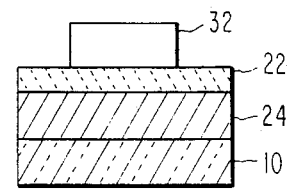

FIG. 7 shows an analysis film having a layer structure comprising support 10 having provided thereon, in sequence, dye fixing layer 24 containing an anionic polymer, TA substrate-POP-color forming reaction layer 22 containing three of the TA substrate layer, the POP composition and the color indicator for detecting hydrogen peroxide and further thereon, in close contact therewith, a porous layer having a definite area, i.e., definite-area porous layer 32—which is porous and determined so as to supply a liquid sample thereto in an amount greater than that of water which can be retained in the porous layer. In more detail, the porous layer has a definite area so that an amount of a liquid sample held in the porous layer is determined by the definite area and the thus determined amount of the liquid sample is transferred to a layer therebeneath (ordinarily a reagent layer) in the same amount and area as in the porous layer, since a possible expansion of the porous layer due to holding the liquid sample is negligible in the width direction when compared to the thickness direction.

It is sufficient that the porous layer has voids to provide transport of the liquid sample but in general, it is preferred that a void volume of the porous layer be in a range of from about 30 to about 85%. Void volume can be calculated by the technique described in Chalkley, *Journal of the National Cancer Institute*, vol. 4, page 47 (1943) and by direct weighing and determining the ratio of actual weight of the structure to the weight of solid material equal in volume to that of the structure. The analysis film comprising the definite area-porous layer is particularly suited for quantitatively assaying transaminase activity in an aqueous liquid sample containing a minor amount of transaminase. A light reflecting layer (or a light blocking layer) can be provided between the TA substrate-POP-color forming reaction layer and the definite area-porous layer. Further, the relative location of the TA substrate-POP-color forming reaction layer to the dye fixing layer can be reversed, as in the case of the analysis film shown in FIG. 6. In place of TA substrate-POP-color forming reaction layer 22, a POP-color forming reaction layer obtained by impregnating the interior of the definite area-porous layer with the TA substrate composition can also be provided.

Figure 8:
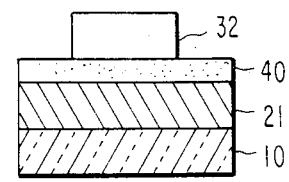

FIG. 8 shows an analysis film having a layer structure comprising support 10 having provided thereon, in sequence, POP-color forming reaction-dye fixing layer 21 containing three of the POP composition, the color indicator for detecting hydrogen peroxide and an anionic polymer, ligh reflecting layer (or light blocking layer) 40 and definite area-porous layer 32. It is also possible to incorporate the TA substrate into the definite area-porous layer and oxaloacetate decarboxylase into the POP-color forming reaction-dye fixing layer (in the case of an analysis film for assaying GOT). In FIGS. 7 and 8, the definite area-porous layer is illustrated so as to be smaller than the remaining layers. However, it is sufficient that the definite area-porous layer be of such a shape and size that are not wider than those of any one of the reagent layers and accordingly, be in the same shape and size as those of any one of the reagent layers without any difficulty.

As supports for the quantitative analysis films as shown in FIGS. 3 through 8, films or sheets of a variety of polymers such as polyethylene terephthalate, cellulose esters (cellulose diacetate, cellulose triacetate, cellulose acetate propionate, etc.), polycarbonates (polycarbonate of bisphenol A, etc.), polymethyl methacrylate, polystyrene, etc., having a thickness of about 25 μm to about 0.3 mm, preferably about 50 μm to about 0.2 mm, can be employed.

Supports which are colorless transparent or transparent to light having wavelengths which the cationic dye formed from the color indicator for detecting hydrogen peroxide absorbs can be employed. In addition, supports which are rendered light-blocking by incorporating pigments therein (e.g., finely divided titanium oxide powder, finely divided barium sulfate powder, finely divided zinc oxide powder, carbon black), etc., can also be employed. In the case that light-blocking supports are employed, colorimetric measurement can be performed after stripping off and removing the support upon colorimetric measurement by measuring reflection light from the side free of the support. The use of a light-blocking support is advantageous in the case where reagent components liable to be photodecomposed are incorporated into a reagent layer, a color-forming reaction layer or a dye-fixing layer.

Preferred embodiments of the analysis film in accordance with the present invention include a layer structure comprising two reagents layers composed of a TA substrate layer and a POP-color forming reaction-dye fixing layer and a layer structure comprising three reagent layers composed of a TA substrate layer, a POP-color forming reaction layer and a dye fixing layer. In the latter, it is preferred that an anionic polymer be contained only in the dye fixing layer and in both the POP-color forming reaction layer and the dye fixing layer.

In the case that the quantitative analysis film of the present invention—including the embodiments shown in FIGS. 2 through 8—takes a multi-layered composite structure, methods as disclosed in Japanese Patent Application (OPI) Nos. 53888/74, 40191/76, 90859/80 and 164356/80, Japanese Patent Application No. 140532/80, Japanese Patent Application (OPI) Nos. 26428/80 and 26429/80, Japanese Utility Model Application No. 120299/80, etc., described above can be used to form the same; alternatively, the quantitative analysis film can be prepared using known various coating techniques established as methods for preparing conventional color photographic light sensitive materials, instant black-and-white or color photographic light sensitive materials as they are or by slightly modifying the same.

Having thus generally described the invention, the following Examples are given to further illustrate the same.

EXAMPLE 1

Onto a colorless transparent polyethylene terephthalate (PET) film for a photographic support, an aqueous solution containing an isoelectric amount of gelatin and potassium polystyrene-4-sulfonate was coated in a dry thickness of 5 μm. After drying, a dye fixing layer was provided thereon.

A coating solution containing the POP composition and the color indicator for detecting hydrogen peroxide having the following composition was prepared:

| Composition of Coating Solution for POP-Color Forming Reaction Layer: | |
|---|---|
| N,N—Bis(β-hydroxyethyl)-m-toluidine | 5.6 mg |
| 4-Aminoantipyrine | 8.0 mg |
| Gelatin | 500 mg |
| Peroxidase | 300 Units |
| Pyruvic acid oxidase | 80 Units |
| FAD | $7.5 \times 10^{-3}$ mg |
| Thiamine pyrophosphate (TDP) | 3 mg |
| Manganese(II) chloride | 2.9 mg |
| Hydrogen disodium phosphate. 12H$_2$O | 109 mg |
| Dihydrogen sodium phosphate. 2H$_2$O | 30 mg |
| Water | 3000 mg |
| Surfactant 10G$^R$ (tradename, made by Olien Co., Ltd., 50 wt % aq. solution containing a compound having the following formula: | 4 mg |

$$C_9H_{19}\!-\!\!\left\langle\:\right\rangle\!-\!O(CH_2CHCH_2O)_{\overline{10}}\!-\!H)$$
$$\underset{OH}{|}$$

| | |
|---|---|
| 1 wt % aq. solution of bis-(vinylsulfonylmethyl)ether | 500 mg: |

The coating solution for the POP-color forming reaction layer was coated onto the dye fixing layer in a dry thickness of 15 μm and dried.

A solution containing a GPT substrate composition having the following formulation was prepared:

| Composition of Solution for GPT Substrate Layer: | |
|---|---|
| α-Ketoglutaric acid | 150 mg |
| L-Alanine | 3 g |
| Hydrogen disodium phosphate. 12H$_2$O | 2.18 g |
| Dihydrogen sodium phosphate.2H$_2$O | 0.60 g |
| Polyacrylamide, 5 wt % aq. solution | 5 g |

-continued

| Composition of Solution for GPT Substrate Layer: | |
|---|---|
| Water | 45 g |
| Surfactant 10G (50 wt % aq. solution) | 200 mg |

A filter paper (thickness of 200 μm, weight of 33 g/m$^2$) for electrophoresis having a smooth surface was impregnated with the solution for the GPT substrate layer. Then, an excess of the solution was squeezed out by passing the filter paper between silicone rubber-made rollers having a roller distance of 300 μm. The filter paper was placed on the surface of a flat glass plate and subjected to natural drying. The GPT substrate composition with which the filter paper was impregnated was uniformly distributed in the filter paper.

The GPT substrate composition-impregnated filter paper was put on and lightly pressed on the POP-color forming reaction layer which had been previously moistened with a 50-fold diluted aqueous solution of Surfactant 10G to thereby fix the filter paper as a porous layer containing the TA substrate composition. Thus, an analysis film for assaying GPT was obtained.

The thus obtained analysis film was cut into a circular shape having a diameter of 9 mm and aqueous solutions of GPT enzyme having various concentrations were dropped on the porous layer (filter paper) to perform the assay.

The assay was performed as follows: 20 μl of saline containing GPT in a proportion of 46 IU/l was dropped on the analysis film. The analysis film was put in a plastic sealable slide for preventing evaporation of moisture and incubated at 37° C. Color density change with the passage of time was measured using a reflection densitometer. The results are shown in the table below.

TABLE 1

| Incubation Time (min.) | Optical Density |
|---|---|
| 5 | 0.35 |
| 10 | 0.49 |
| 15 | 0.61 |
| 20 | 0.74 |

Further, 20 μl of saline having various GPT activities was dropped on the analysis film and the analysis film was incubated at 37° C. for 10 mins. Reflected optical density was measured 10 minutes thereafter. The results are shown in the table below.

TABLE 2

| GPT Activity (IU/l) | 20 | 46 | 72 | 100 |
|---|---|---|---|---|
| Reflection Optical Density | 0.33 | 0.49 | 0.68 | 0.82 |

From the results above, it can be seen that there is almost a linear relationship between GPT activity and reflection optical density. It is thus clear that GPT activity can be measured using this analysis film in accordance with colorimetry by measuring reflection light.

EXAMPLE 2

As in Example 1, a filter paper, a glass fiber filter paper, cotton cloth, PET/cotton-mixed cloth, membrane filter, etc.—which had been impregnated with the solution of GPT substrate composition—were put on and adhered, respectively, to the POP-color forming reaction layer of the analysis film composed of the dye fixing layer and the POP-color forming reaction layer prepared as in Example 1. Thus, a multilayer analysis film for assaying GPT activity was obtained.

Color was formed with each of the analysis films in a manner similar to Example 1. Reflection optical density which correlated to GPT activity was observed.

EXAMPLE 3

In a manner similar to Example 1, an analysis film composed of the dye fixing layer and the POP-color forming reaction layer was prepared. An aqueous dispersion of finely divided titanium dioxide powder in gelatin was coated on the POP-color forming reaction layer as a light blocking layer in a dry thickness of 5 μm followed by drying.

| Composition of Aqueous Dispersion for Light Blocking Layer: | |
|---|---|
| TiO$_2$ fine powder | 19.5 g |
| Gelatin | 6.8 g |
| Surfactant 10G ® | 0.9 g |
| Water | 87 g |

Then, an analysis film for assaying GPT activity was prepared in a manner similar to Example 1. Saline containing various concentrations of GPT was dropped on the analysis film as in Example 1 to form a color. Color formation could be observed at the white background. The measurement of reflection optical density showed almost similar results as in Example 1.

EXAMPLE 4

To a coating solution for a POP-color forming reaction layer having the same composition as in Example 1, 400 μl of a 5% aqueous solution of an anionic polymer of pH 6.5 to 7.0 obtained by hydrolyzing a methyl vinyl ether-maleic anhydride copolymer (Gantrez AN 169 ®, manufactured by GAF Corporation) with an equimolar amount of potassium hydroxide was added.

Then, the coating solution was:
(A) coated onto a photographic support made of a colorless transparent PET film, the adhesion of which surface had been improved;
(B) coated onto the dye fixing layer as in Example 1; and
(C) for comparison, a coating solution for a POP-color forming reaction layer having the same composition as in Example 1 was coated onto the same photographic support as (A) above.

Further, a light blocking layer was coated onto each of the multilayer analysis films (A), (B) and (C) in a manner as in Example 3 and then dried to obtain analysis films (A), (B) and (C).

Each of the analysis films was cut into a 15 mm square and a circular filter paper (thickness of 200 μm, a definite area-porous layer) having a diameter of 9 mm was placed thereon. On each of the analysis films, 20 μl of an aqueous solution of potassium pyruvate having a concentration of 10$^{-3}$ mole/l was dropped. After allowing to stand for 10 mins. at room temperature (25° C.), the reflection optical density of the formed color was measured. The results are shown in the table below.

TABLE 3

| Analysis Film | Optical Density |
|---|---|
| (A) | 1.05 |
| (B) | 1.23 |
| (C) | 0.54 |

With analysis film (A), the formed cationic dye was fixed with the anionic polymer in the POP-color forming reaction layer or in the dye fixing layer; the formed cationic dye was fixed with the anionic polymer in the dye fixing layer in the case of analysis film (B). Accordingly, any one of the cationic dyes was hardly diffused into the filter paper (definite area-porous layer) so that the optical densities determined by measuring reflection light were high. However, with analysis film (C), a part of the formed cationic dye was diffused into the filter paper. The cationic dye diffused into the filter paper did not contribute to the optical density of the formed color so that the optical density obtained by measuring reflection light was markedly poor. By this experiment, it is clearly understood that anionic polymers contained in the analysis film of the present invention could effectively fix cationic dyes.

EXAMPLE 5

A coating solution of an enzyme substrate composition was coated onto multilayer analysis film (B) (multilayer analysis film (B) where no filter paper was provided on the light blocking layer) obtained in Example 4, in a dry thickness of 80 μm and then dried to form a GOT substrate layer.

| Coating Solution of GOT Enzyme Substrate Composition: | |
|---|---|
| L-Aspargic acid | 2.5 g |
| α-Ketoglutaric acid | 120 mg |
| Hydrogen disodium phosphate. 12H$_2$O | 1.09 g |
| Dihydrogen sodium phosphate. 2H$_2$O | 0.30 g |
| Polyacrylamide, 5 wt % aq. solution | 100 g |
| Nonionic surface active agent (isooctylphenyl-polyethoxyethanol, tradename "Triton X-100", made by Rohm and Haas Co., Ltd.) | 100 mg |

The GOT substrate layer of the thus prepared multilayer film was moistened with a 1 wt% Triton X-100 aqueous solution and a membrane filter having a thickness of 180 μm and an area of 50 mm$^2$ was lightly pressed on and adhered to the GOT substrate layer to obtain an analysis film for assaying GOT activity.

Onto the definite area-porous layer of the thus prepared analysis film, 10 μl. each of aqueous saline solutions of GOT (containing 40, 70, 105 and 205 IU/l of GOT) was dropped followed by incubation at 37° C. for 20 mins. Thereafter, optical reflection densities were measured from the PET film side. The optical densities obtained are shown in the table below.

TABLE 4

| GOT Activity (IU/l) | 40 | 70 | 105 | 205 |
|---|---|---|---|---|
| Reflection Optical Density | 0.31 | 0.62 | 0.78 | 1.18 |

From the results above, it is understood that there is a correlation between GOT activity and reflection optical density and GOT activity can be quantitatively determined using this analysis film based on the GOT activity-reflection optical density based on a calibration curve.

EXAMPLE 6

Normal blood serum was dropped on the analysis film for assaying GPT and the analysis film for assaying GOT obtained in Examples 1 and 5, respectively and testing was performed. As a result, an average of GPT activities showed 0.30 in reflection optical density and an average of GOT activities showed 0.28 in reflection optical density, when n is 5.

EXAMPLE 7

Four kinds of porous materials, i.e., a filter paper having a thickness of 185 μm, a membrane filter (average pore size of 5 μm, made by Fuji Photo Film Co., Ltd., tradename, "Microfilter FM ® 500) having a thickness of 150 μm, cotton cloth (braodcloth) of 100 counts and a glass fiber filter paper having a thickness of 200 μm, were impregnated with an aqueous solution of a GOT substrate composition having a formulation below, respectively, and then dried.

| Aqueous Solution of GOT Enzyme Substrate Composition: | |
|---|---|
| L-Aspargic acid | 2.5 g |
| α-Ketoglutaric acid | 120 mg |
| Hydrogen disodium phosphate. 12H$_2$O | 1.09 g |
| Dihydrogen sodium phosphate 2H$_2$O | 0.30 g |
| Polyacrylamide, 5 wt % aq. solution | 5 g |
| Water | 40 g |
| Surfactant 10G 50% aq. solution | 200 mg |

Then, analysis film (B) (multilayer analysis film (B) where no filter paper was provided on the light blocking layer) obtained in Example 4 was moistened with a 50-fold diluted Surfactant 10G aqueous solution and each of the resulting GOT substrate composition-impregnated porous materials cut into an area of 100 mm$^2$ was lightly pressed thereon and fixed thereto to prepare multilayer analysis films for assaying GOT having definite area-porous layers impregnated with the GOT substrate composition.

Onto the definite area-porous layer of each of these four analysis films, an aqueous saline solution of GOT having 50 IU/l potency was dropped, respectively, by 40 μl for the definite area-porous layer obtained from broadcloth and by 20 μl each for the fixed area-porous layer obtained from the other three porous materials. Incubation was performed for 60 mins. at 37° C., during which optical densities of the formed colors were measured at a 5 minute interval of the incubation from the PET film side. It was noted that optical densities of the formed colors increased in a linear relation during the incubation time from 5 mins. to 30 mins. with all of the four analysis films.

From the results above, it is evident that by the use of these four multilayer analysis films for assaying GOT, GOT activity could be quantitatively determined in an incubation time ranging of from 5 mins. to 30 mins., based on a calibration curve.

While the invention has been described in detail and with reference to specific embodiments thereof, it will be apparent to one skilled in the art that various changes and modifications can be made therein without departing from the spirit and scope thereof.

What is claimed is:

1. An analysis film comprising a reagent layer containing a transaminase substrate composition, a pyruvic acid oxidase composition, a cationic dye-forming color indicator for detecting hydrogen peroxide, and an anionic polymer containing a sulfonate group capable of reacting with formed cationic dye to fix the formed dye.

2. The analysis film of claim 1 wherein said pyruvic acid oxidase composition includes pyruvic acid oxidase, a phosphate source compound, flavine adenine dinucleotide, thiamine pyrophosphate, and a divalent or trivalent metal ion.

3. The analysis film of claim 2 wherein said color indicator composition for detecting hydrogen peroxide comprises a substance having peroxidase activity, a hydrogen donor and a coupler.

4. The analysis film of any one of claims 1, 2 or 3 wherein said reagent layer is a single layer.

5. The analysis film of any one of claims 1, 2 or 3 wherein said reagent layer is composed of at least two layers one of which is a transaminase substrate layer containing a transaminase substrate and one of which is a pyruvic acid oxidase color forming reaction dye fixing layer comprising a pyruvic acid oxidase composition, a color indicator and an anionic polymer.

6. The analysis film of any one of claims 1, 2 or 3 wherein said reagent layer comprises at least two layers one of which is a dye fixing layer containing an anionic polymer and one of which is a transaminase substrate-pyruvic acid oxidase color forming reaction layer comprising a transaminase substrate composition, a pyruvic acid oxidase composition and a color indicator.

7. The analysis film of any one of claims 1, 2 or 3 wherein said reagent layer possesses a support on one surface thereof and a porous layer on the other surface thereof and said porous layer is adhered to said reagent layer in a fluid contact as an integral form.

* * * * *